(12) United States Patent
Lehman et al.

(10) Patent No.: US 7,790,825 B2
(45) Date of Patent: Sep. 7, 2010

(54) HIGH REFRACTIVE INDEX OPHTHALMIC DEVICE MATERIALS

(75) Inventors: Chance Lehman, Dallas, TX (US); Charles Freeman, Granbury, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 12/436,022

(22) Filed: May 5, 2009

(65) Prior Publication Data

US 2009/0281209 A1  Nov. 12, 2009

Related U.S. Application Data

(60) Provisional application No. 61/050,866, filed on May 6, 2008.

(51) Int. Cl.
- C08F 18/10 (2006.01)
- C08F 20/18 (2006.01)
- C08F 220/18 (2006.01)
- C08F 220/10 (2006.01)
- A61F 2/16 (2006.01)
- G02B 1/04 (2006.01)

(52) U.S. Cl. .............. 526/326; 526/319; 526/328.5; 526/329.1; 523/106; 623/6.11

(58) Field of Classification Search ............... 523/105, 523/106, 107, 108; 351/160 H, 160 R; 526/326, 526/319, 329.1, 328.5; 623/6.11
See application file for complete search history.

(56) References Cited

U.S. PATENT DOCUMENTS

| | | | |
|---|---|---|---|
| 4,304,895 A | 12/1981 | Loshaek | |
| 4,528,311 A | 7/1985 | Beard et al. | |
| 4,780,488 A | 10/1988 | Su et al. | |
| 4,857,606 A | 8/1989 | Su et al. | |
| 5,039,769 A | 8/1991 | Molock et al. | |
| 5,070,166 A | 12/1991 | Su et al. | |
| 5,070,169 A | 12/1991 | Robertson et al. | |
| 5,070,170 A | 12/1991 | Robertson et al. | |
| 5,077,033 A | 12/1991 | Viegas et al. | |
| 5,290,892 A | 3/1994 | Namdaran et al. | |
| 5,470,932 A | 11/1995 | Jinkerson | |
| 5,891,931 A * | 4/1999 | Leboeuf et al. | ............... 522/64 |
| 6,528,602 B1 | 3/2003 | Freeman et al. | |
| 6,534,559 B1 | 3/2003 | Vanderlaan et al. | |
| 6,534,591 B2 | 3/2003 | Rhee et al. | |
| 6,544,953 B2 | 4/2003 | Tsuzuki et al. | |
| 6,555,030 B1 | 4/2003 | Weinschenk, III | |
| 6,635,731 B2 | 10/2003 | Mentak | |
| 6,635,732 B2 | 10/2003 | Mentak | |
| 6,653,422 B2 | 11/2003 | Freeman et al. | |
| 6,657,029 B2 | 12/2003 | Vanderbilt | |
| 6,657,030 B2 | 12/2003 | Vanderbilt | |
| 6,657,032 B2 | 12/2003 | Vanderbilt | |
| 6,673,886 B2 | 1/2004 | Vanderbilt | |
| 6,703,466 B1 * | 3/2004 | Karakelle et al. | ........... 526/259 |
| 6,713,583 B2 | 3/2004 | Liao et al. | |
| 6,780,899 B2 | 8/2004 | Liao et al. | |
| 6,939,485 B2 | 9/2005 | Kish | |
| 7,037,469 B2 | 5/2006 | Hu et al. | |
| 7,176,256 B2 | 2/2007 | Rhee et al. | |
| 7,247,270 B2 | 7/2007 | Hu et al. | |
| 2001/0037150 A1 | 11/2001 | Chan et al. | |
| 2002/0128417 A1 * | 9/2002 | Mentak | ................... 526/318.1 |
| 2003/0017797 A1 * | 1/2003 | Kendall et al. | .............. 451/526 |
| 2003/0175503 A1 * | 9/2003 | Lucast et al. | ................ 428/343 |
| 2004/0142829 A1 * | 7/2004 | Tsao et al. | .................. 510/112 |
| 2004/0144726 A1 * | 7/2004 | Chmelka et al. | ............ 210/660 |
| 2006/0118493 A9 * | 6/2006 | Chmelka et al. | ............ 210/660 |
| 2006/0205621 A1 | 9/2006 | Borazjani et al. | |
| 2006/0275342 A1 | 12/2006 | Lindhardt et al. | |
| 2007/0179224 A1 * | 8/2007 | Fanayar et al. | .............. 524/100 |
| 2007/0196329 A1 | 8/2007 | Xia et al. | |
| 2009/0043006 A1 | 2/2009 | Freeman | |

FOREIGN PATENT DOCUMENTS

| | | |
|---|---|---|
| WO | WO9908136 A1 | 2/1999 |
| WO | WO9953347 A1 | 10/1999 |
| WO | WO0118078 A1 | 3/2001 |
| WO | WO0149240 A2 | 7/2001 |
| WO | WO2004030715 A1 | 4/2004 |
| WO | WO2009015256 A2 | 1/2009 |

\* cited by examiner

*Primary Examiner*—Mark Eashoo
*Assistant Examiner*—Mike Pepitone
(74) *Attorney, Agent, or Firm*—Patrick M. Ryan

(57) ABSTRACT

High refractive index copolymers suitable for use in ophthalmic devices are disclosed. The copolymers comprise a single aryl hydrophobic monomer as a device forming monomer. In addition, the copolymers comprise a non-polymerizable block copolymer surfactant. The copolymers have a reduced tendency to form glistenings when stored in water at physiological temperatures.

14 Claims, No Drawings

HIGH REFRACTIVE INDEX OPHTHALMIC DEVICE MATERIALS

CROSS-REFERENCE TO RELATED APPLICATIONS

This application claims priority to U.S. Provisional Patent Application No. 61/050,866 filed May 6, 2008, the entire contents of which are incorporated herein by reference.

FIELD OF THE INVENTION

This invention relates to high refractive index polymers and their use in ophthalmic lenses, particularly intraocular lenses that can be inserted through small incisions.

BACKGROUND OF THE INVENTION

High refractive index acrylic materials are known for use in intraocular lenses (IOLs). For example, U.S. Pat. No. 5,290,892 discloses high refractive index acrylic materials suitable for use as IOL materials. The materials are foldable and thus capable of being inserted through small incisions. These acrylic materials contain, as principal components, two aryl acrylic monomers.

In some cases, foldable acrylic intraocular lenses develop "glistenings" or "vacuoles" when implanted in humans or soaked in water at physiological temperatures. These microvacuoles appear to be pockets of water approximately 1 μm or greater in diameter. Glistenings are often too small to be seen by the naked eye, but are sometimes observed using a slit-lamp. Although glistenings have no detrimental effect on the function or performance of IOLs made from acrylic materials, it is nevertheless cosmetically desirable to minimize or eliminate them.

Published U.S. Patent Application 2006/0275342 A1 discloses ophthalmic device materials, including IOL materials, containing less than 15% by weight of certain polymerizable surfactants. The polymerizable surfactants are poloxamers and poloxamines, which are generally available under the PLURONIC and TETRONIC tradenames. One advantage of adding such polymerizable surfactants as comonomers in forming polymeric devices is said to be changed or improved device surface properties, such as lipid or protein uptake. It was determined that the functionalized surfactants did not affect mechanical properties of the device materials as the addition of the polymerizable surfactants produced no real change in the modulus or tear strength (see Example 17 of 2006/0275342 A1). The surfactants are chemically modified to make them polymerizable as comonomers. When unmodified surfactants were incorporated into a hydrogel contact lens material during polymerization, it was noted that upon hydration the lenses would become cloudy. When methacrylated counterparts of the unmodified surfactants were used, however, optical clarity was maintained after hydration (see Example 16 and FIGS. 6-8 of 2006/0275342 A1).

SUMMARY OF THE INVENTION

This invention is directed to ophthalmic device materials that do not contain glistenings. The ophthalmic device materials comprise a) device forming monomers consisting essentially of a single polymerizable monomer of the structure:

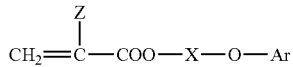

wherein:
Z is H or $CH_3$;
X is $(CH_2)_m$ or $O(CH_2CH_2O)_n$;
m is 2-6;
n is 1-6; and
Ar is phenyl which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_5$;

b) a polymerizable cross-linking agent; and c) a non-polymerizable propylene oxide-ethylene oxide-propylene oxide block copolymer surfactant having a molecular weight (average) of approximately 3600 and an ethylene oxide unit content of approximately 40% by weight or a non-polymerizable ethylene oxide-propylene oxide-ethylene oxide block copolymer surfactant having a molecular weight (average) of approximately 5900 and an ethylene oxide unit content of approximately 40% by weight.

These device materials can be used to form intraocular lenses that have high refractive indexes, are flexible and transparent, can be inserted into the eye through a relatively small incision, and recover their original shape after having been inserted. Moreover, IOLs made from these materials are free or substantially free of glistenings compared to otherwise identical materials lacking the non-polymerizable surfactant.

Among other factors, the present invention is based upon the finding that the ophthalmic device materials obtained by copolymerizing one monomer of structure (I) and a cross-linking agent with the specified non-polymerizable surfactants are clear. Additionally, unlike when other propylene oxide-ethylene oxide-propylene oxide block copolymer surfactants are added to a monomer of structure (I) to obtain ophthalmic device materials, when a non-polymerizable propylene oxide-ethylene oxide-propylene oxide block copolymer surfactant having an average molecular weight of approximately 3600 and an ethylene oxide unit content of approximately 40% by weight or a non-polymerizable ethylene oxide-propylene oxide-ethylene oxide block copolymer surfactant having an average molecular weight of approximately 5900 and an ethylene oxide content of approximately 40% by weight is added, the device materials are free or substantially free of glistenings.

DETAILED DESCRIPTION OF THE INVENTION

The ophthalmic device materials of the present invention comprise device forming monomers consisting essentially of a single monomer of the structure:

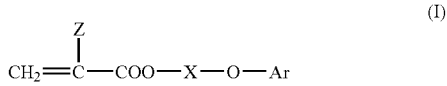

wherein:

Z is H or $CH_3$;

X is $(CH_2)_m$ or $O(CH_2CH_2O)_n$;

m is 2-6;

n is 1-6; and

Ar is phenyl which can be unsubstituted or substituted with $CH_3$, $C_2H_5$, $n\text{-}C_3H_7$, $iso\text{-}C_3H_7$, $OCH_3$, $C_6H_{11}$, Cl, Br, $C_6H_5$, or $CH_2C_6H_5$;

Monomers of structure (I) can be made by methods known in the art. For example, the conjugate alcohol of the desired monomer can be combined in a reaction vessel with methyl acrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding acrylic acid to the conjugate alcohol and catalyzing with a carbodiimide or mixing the conjugate alcohol with acryloyl chloride and a base such as pyridine or triethylamine.

Suitable monomers of structure (I) include, but are not limited to: 2-phenoxyethyl acrylate; 3-phenoxypropyl acrylate; 4-phenoxybutyl acrylate; polyethylene glycol phenyl ether acrylate; and their corresponding methacrylates.

Preferred monomers of structure (I) are those wherein X is $(CH_2)_m$; m is 2-4, and Ar is phenyl. Most preferred is 2-phenoxyethyl acrylate.

The total amount of the monomer of structure (I) contained in the device materials of the present invention is generally about 75% by weight or more, and is preferably about 80-90 % by weight, of the total amount of polymerizable components of the ophthalmic device materials. Most preferably, the total amount of monomer of structure (I) contained in the device materials of the present invention is 87-90 % by weight.

The ophthalmic device materials of the present invention also contain a polymerizable cross-linking agent. The cross-linking agent may be any terminally ethylenically unsaturated compound having more than one unsaturated group. Suitable cross-linking agents include, for example: ethylene glycol dimethacrylate, diethylene glycol dimethacrylate, allyl methacrylate, 1,3-propanediol dimethacrylate, allyl methacrylate, 1,6-hexanediol dimethacrylate, 1,4-butanediol dimethacrylate, and their corresponding acrylates. Preferred cross-linking agents are ethylene glycol dimethacrylate (EGDMA); 1,4-butanediol diacrylate (BDDA); and 1,6-hexanediol diacrylate. In general, the amount of any cross-linking agent used in the device materials of the present invention will be 5% by weight or less, preferably 1-2% by weight, of the polymerizable components of the ophthalmic device materials.

In addition to the single monomer of structure (I) and a cross-linking agent, the copolymers of the present invention also contain a non-polymerizable block copolymer surfactant selected from the group consisting of: a propylene oxide-ethylene oxide-propylene oxide block copolymer surfactant having an average molecular weight of approximately 3600 and an ethylene oxide unit content of approximately 40% by weight and an ethylene oxide-propylene oxide-ethylene oxide block copolymer surfactant having an average molecular weight of approximately 5900 and a ethylene oxide unit content of approximately 40% by weight. Such surfactants are commercially available from BASF under the tradenames Pluronic® 25R4 and Pluronic® P104. The amount of non-polymerizable block copolymer surfactant contained in the ophthalmic device materials of the present invention is generally 5-15% by weight, and is preferably 9-11% by weight.

The proportions of the monomers to be included in the copolymers of the present invention are preferably chosen so that the copolymer has a glass transition temperature ($T_g$) not greater than about 37° C., which is normal human body temperature. Copolymers having glass transition temperatures higher than 37° C. are not suitable for use in foldable IOLs; such lenses could only be rolled or folded at temperatures above 37° C. and would not unroll or unfold at normal body temperature. It is preferred to use copolymers having a glass transition temperature somewhat below normal body temperature and no greater than normal room temperature, e.g., about 20-25° C., in order that IOLs made of such copolymers can be rolled or folded conveniently at room temperature. $T_g$ is measured by differential scanning calorimetry at 10° C./min., and is determined at the midpoint of the transition of the heat flux curve.

For IOLs and other implant applications, the materials of the present invention preferably exhibit sufficient strength to allow devices made of them to be folded or manipulated without fracturing. Thus the copolymers of the present invention will have an elongation of at least 80%, preferably at least 100%, and most preferably between 110 and 200%. This property indicates that lenses made of such materials generally will not crack, tear or split when folded. Elongation of polymer samples is determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at ambient conditions using an Instron Material Tester (Model No. 4442 or equivalent) with a 50 Netwon load cell. The grip distance is set at 14 mm and a crosshead speed is set at 500 mm/minute and the sample is pulled until failure. The elongation (strain) is reported as a fraction of the displacement at failure to the original grip distance. Since the materials to be tested are essentially soft elastomers, loading them into the Instron machine tends to make them buckle. To remove the slack in the material sample a pre-load is placed upon the sample. This helps to reduce the slack and provide a more consistent reading. Once the sample is pre-loaded to a desired value (typically 0.03 to 0.05 N) the strain is set to zero and the test begun.

When the ophthalmic device materials of the present invention are used to make IOLs, the materials preferably have a refractive index of 1.53 or greater in the fully hydrated state as measured by a refractometer at 37° C.±2° C.

IOLs made of the ophthalmic device materials of the present invention are free or substantially free of glistenings when measured according to the following test ("the Glistening Test"). The presence of glistenings is measured by placement of a lens or disk sample into a vial and adding deionized water or a balanced salt solution. The vial is then placed into a water bath preheated to 45° C. Samples are to be maintained in the bath for 24±2 hours. The vial is then removed from the water bath and allowed to equilibrate at room temperature for 2±0.5 hours. The sample is removed from the vial and placed on a microscope slide. The sample is inspected visually in various on angle or off angle lighting to evaluate clarity. Visualization of glistenings is done with light microscopy using a magnification of 10 to 100×. A sample is judged to be free of glistenings if, at 10-100× magnification, the number of glistenings detected in the eyepiece is zero. A sample is judged to be substantially free of glistenings if, at 10-100× magnification, the number of glistenings detected in the eyepiece is less than about $2/mm^3$. It is often very difficult to detect glistenings, so the sample is rastered throughout the entire volume of the lens, varying the magnification levels (10-100×), the aperture iris diaphragm, and the field conditions (using both bright field and dark field conditions) in an attempt to detect the presence of glistenings.

An ultra-violet absorbing material may also be included in the materials of the present invention. The ultraviolet absorbing material can be any compound which absorbs ultraviolet light, i.e., light having a wavelength shorter than about 400 nm, but does not absorb any substantial amount of visible light. The ultraviolet absorbing compound is incorporated into the monomer mixture and is entrapped in the polymer matrix when the monomer mixture is polymerized. Suitable ultraviolet absorbing compounds include substituted benzophenones, such as 2-hydroxybenzophenone, and 2-(2-hydroxyphenyl )benzotriazoles. It is preferred to use an ultraviolet absorbing compound which is copolymerizable with the monomers and is thereby covalently bound to the polymer matrix. In this way possible leaching of the ultraviolet absorbing compound out of the lens and into the interior of the eye is minimized. Suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311. The most preferred ultraviolet absorbing compounds are 2-(2'-hydroxy-3'-methallyl-5'-methyl phenyl) benzotriazole and 2-(3'-tert-butyl-2'-hydroxy-5'-methacryloylpropoxyphenyl)-5-methoxy-2H-benzotriazole In addition to ultraviolet absorbing materials, ophthalmic devices made of the copolymers of the present invention may include colored dyes, such as the yellow dyes disclosed in U.S. Pat. No. 5,470,932.

The copolymers of this invention are prepared by conventional polymerization methods. For example, a mixture of the liquid monomer of structure (I) and a cross-linking agent in the desired proportions, together with one of the specified non-polymerizable surfactants, a UV absorber, a yellow dye, and a conventional thermal free-radical initiator, is prepared. The mixture can then be introduced into a mold of desired shape, and the polymerization carried out by heating to activate the initiator. Typical thermal free radical initiators include peroxides, such as benzophenone peroxide, peroxycarbonates, such as bis-(4-t-butylcyclohexyl) peroxydicarbonate, azonitriles, such as azobisisobutyronitrile, and the like. A preferred initiator is tert-butyl peroxy-2-ethylhexanoate (T21s). Alternatively, the monomers can be photopolymerized by using a mold which is transparent to actinic radiation of a wavelength capable of initiating polymerization of these acrylic monomers by itself. Conventional photoinitiator compounds, e.g., a benzophenone-type photoinitiator, can also be introduced to facilitate the polymerization.

Once the ophthalmic device materials of the present invention have been cured, they are extracted in a suitable solvent to remove as much of the unreacted components of the materials as possible. Examples of suitable solvents include acetone, methanol, and cyclohexane. A preferred solvent for extraction is acetone.

IOLs constructed of the disclosed ophthalmic device materials can be of any design capable of being rolled or folded into a small cross section that can fit through a relatively smaller incision. For example, the IOLs can be of what is known as a one piece or multipiece design. Typically, an IOL comprises an optic and at least one haptic. The optic is that portion which serves as the lens and the haptics are attached to the optic and are like arms which hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the ophthalmic device materials of the present invention are also suitable for use in other devices, including contact lenses, keratoprostheses, intracorneal lenses, corneal inlays or rings, and glaucoma filtration devices.

The invention will be further illustrated by the following examples which are intended to be illustrative, but not limiting.

EXAMPLE 1

The device materials identified in Table 1 below were prepared by dissolving the indicated ingredients in a 20 ml glass vial and mixing them with a vortex mixer. POEA=2-phenoxyethyl acrylate. BDDA=1,4-butanediol diacrylate. L31, L43, L61, L64, L81, L92, L101, F87, F88, F98, F127, P84, P104, 10R5, 17R2, 17R4, 25R2, 25R4, 31R1=Pluronicsurfactant type by BASF tradename. Each formulation was purged with nitrogen for 2 minutes, placed under high vacuum (<0.5 mm Hg) for 2 minutes, injected through a 0.2 micron PTFE filter into standard polypropylene slab molds, and then heated at 70° C. for 2 hours, ramped to 110° C. during 10 minutes, and post cured at 110° C. for 1 hour. Three-five slabs were weighed for % extractables. The polymer slabs were extracted in acetone for at least 16 hours at ambient temperature with one solvent change out after the first hour, and then allowed to dry while covered with aluminum foil at ambient temperature for 8 hours. Slabs were further dried under reduced atmosphere at 60° C. for at least 16 hours. Slabs were removed and cooled to room temperature. Previously weighed slabs were weighed again for % extractables. Slabs were hydrated in a water bath at room temperature and 35° C. and the equilibrium water content ("% EWC") at each temperature was determined. The results are shown in Table 2.

TABLE 1

Device Materials

| Sample Name | POEA | BDDA | L31 | L43 | L61 | L64 | L81 | L92 | L101 | F87 | F88 |
|---|---|---|---|---|---|---|---|---|---|---|---|
| L31 | 98.5% | 1.5% | 10.0% | — | — | — | — | — | — | — | — |
| L43 | 98.5% | 1.5% | — | 10.0% | — | — | — | — | — | — | — |
| L61 | 98.5% | 1.5% | — | — | 10.0% | — | — | — | — | — | — |
| L64 | 98.5% | 1.5% | — | — | — | 10.0% | — | — | — | — | — |

TABLE 1-continued

Device Materials

| Sample Name | | | | | | | | | | | |
|---|---|---|---|---|---|---|---|---|---|---|---|
| L81 | 98.5% | 1.5% | — | — | — | — | 10.0% | — | — | — | — |
| L92 | 98.5% | 1.5% | — | — | — | — | — | 10.0% | — | — | — |
| L101 | 98.5% | 1.5% | — | — | — | — | — | — | 10.0% | — | — |
| F87 | 98.5% | 1.5% | — | — | — | — | — | — | — | 10.0% | — |
| F88 | 98.5% | 1.5% | — | — | — | — | — | — | — | — | 10.0% |
| F98 | 98.5% | 1.5% | — | — | — | — | — | — | — | — | — |
| F127 | 98.5% | 1.5% | — | — | — | — | — | — | — | — | — |
| P84 | 98.5% | 1.5% | — | — | — | — | — | — | — | — | — |
| P104 | 98.5% | 1.5% | — | — | — | — | — | — | — | — | — |
| 10R5 | 98.5% | 1.5% | — | — | — | — | — | — | — | — | — |
| 17R2 | 98.5% | 1.5% | — | — | — | — | — | — | — | — | — |
| 17R4 | 98.5% | 1.5% | — | — | — | — | — | — | — | — | — |
| 25R2 | 98.5% | 1.5% | — | — | — | — | — | — | — | — | — |
| 25R4 | 98.5% | 1.5% | — | — | — | — | — | — | — | — | — |
| 31R1 | 98.5% | 1.5% | — | — | — | — | — | — | — | — | — |
| ctrl | 98.5% | 1.5% | — | — | — | — | — | — | — | — | — |

| Sample Name | F98 | F127 | P84 | P104 | 10R5 | 17R2 | 17R4 | 25R2 | 25R4 | 31R1 | CTRL |
|---|---|---|---|---|---|---|---|---|---|---|---|
| L31 | — | — | — | — | — | — | — | — | — | — | — |
| L43 | — | — | — | — | — | — | — | — | — | — | — |
| L61 | — | — | — | — | — | — | — | — | — | — | — |
| L64 | — | — | — | — | — | — | — | — | — | — | — |
| L81 | — | — | — | — | — | — | — | — | — | — | — |
| L92 | — | — | — | — | — | — | — | — | — | — | — |
| L101 | — | — | — | — | — | — | — | — | — | — | — |
| F87 | — | — | — | — | — | — | — | — | — | — | — |
| F88 | — | — | — | — | — | — | — | — | — | — | — |
| F98 | 10.0% | — | — | — | — | — | — | — | — | — | — |
| F127 | — | 10.0% | — | — | — | — | — | — | — | — | — |
| P84 | — | — | 10.0% | — | — | — | — | — | — | — | — |
| P104 | — | — | — | 10.0% | — | — | — | — | — | — | — |
| 10R5 | — | — | — | — | 10.0% | — | — | — | — | — | — |
| 17R2 | — | — | — | — | — | 10.0% | — | — | — | — | — |
| 17R4 | — | — | — | — | — | — | 10.0% | — | — | — | — |
| 25R2 | — | — | — | — | — | — | — | 10.0% | — | — | — |
| 25R4 | — | — | — | — | — | — | — | — | 10.0% | — | — |
| 31R1 | — | — | — | — | — | — | — | — | — | 10.0% | — |
| ctrl | — | — | — | — | — | — | — | — | — | — | — |

TABLE 2

% extractables and % EWC

| Sample | % ext | SD (±) | % EWC (23 C.) | SD (±) | % EWC (35 C.) | SD (±) |
|---|---|---|---|---|---|---|
| L31 | 13.80% | 0.14% | 0.68% | 0.09% | 0.60% | 0.08% |
| L43 | 14.21% | 0.09% | 0.82% | 0.18% | 0.77% | 0.14% |
| L61 | | | | | | |
| L64 | 13.48% | 0.27% | 0.95% | 0.34% | 0.77% | 0.20% |
| L81 | 13.66% | 0.27% | 0.93% | 0.07% | 0.89% | 0.15% |
| L92 | 13.21% | 0.17% | 1.05% | 0.10% | 1.01% | 0.06% |
| L101 | 13.62% | 0.22% | 1.11% | 0.03% | 1.16% | 0.12% |
| F87 | 11.20% | 0.92% | 2.87% | 0.24% | 2.63% | 0.26% |
| F88 | 9.77% | 0.40% | 3.88% | 0.12% | 4.31% | 0.16% |
| F98 | 9.16% | 0.38% | 4.42% | 0.21% | 5.26% | 0.27% |
| F127 | 9.55% | 0.65% | 4.09% | 0.09% | 4.42% | 0.11% |
| P84 | 12.47% | 0.42% | 0.89% | 0.16% | 0.38% | 0.28% |
| P104 | 12.18% | 0.13% | 1.48% | 0.03% | 1.04% | 0.09% |
| 10R5 | 14.12% | 0.43% | 0.44% | 0.05% | 0.12% | 0.22% |
| 17R2 | 12.96% | 0.23% | 0.40% | 0.04% | 0.10% | 0.10% |
| 17R4 | 13.68% | 0.38% | 0.39% | 0.06% | 0.22% | 0.19% |
| 25R2 | 13.60% | 0.33% | 0.54% | 0.08% | 0.28% | 0.02% |
| 25R4 | 13.45% | 0.40% | 0.73% | 0.04% | 0.41% | 0.16% |
| 31R1 | 13.58% | 0.24% | 0.61% | 0.06% | 0.19% | 0.09% |
| ctrl | 5.62% | 0.17% | 0.25% | 0.14% | 0.00% | — |

Tensile bar specimens in the fashion of "dogbones" were cut from each sample group using a die and press. Typically, 3 specimens per slab were prepared and 9 total specimens per formulation. Tensile properties were measured using an Instron 5543 extensometer at 500 mm/min crosshead speed. Stress at break, % strain at break, Young's modulus, the 25% secant modulus, and 100% secant modulus data were obtained. The results are shown in Table 3.

TABLE 3

Tensile properties

| Sample | Stress at Break (MPa) | SD (±) | Strain at Break (%) | SD (±) | Young's Modulus (MPa) | SD (±) | 25% Secant Modulus (MPa) | SD (±) | 100% Secant Modulus (MPa) | SD (±) |
|---|---|---|---|---|---|---|---|---|---|---|
| L31 | 11.51 | 1.17 | 168.8 | 8.3 | 98.63 | 7.15 | 14.37 | 0.75 | 5.25 | 0.18 |
| L43 | 10.17 | 0.66 | 158.6 | 5.4 | 90.37 | 6.70 | 13.42 | 1.00 | 5.14 | 0.16 |
| L61 | 13.36 | — | 174.8 | — | 99.53 | — | 14.87 | — | 5.44 | — |
| L64 | 11.38 | 0.77 | 181.0 | 5.1 | 73.00 | 5.56 | 11.16 | 0.50 | 4.47 | 0.13 |
| L81 | 11.07 | 0.90 | 165.9 | 6.8 | 97.79 | 6.05 | 14.06 | 0.80 | 5.37 | 0.23 |
| L92 | 11.88 | 0.82 | 171.0 | 4.5 | 89.40 | 10.04 | 13.44 | 1.29 | 5.22 | 0.26 |
| L101 | 10.91 | 1.37 | 166.6 | 10.3 | 93.78 | 5.93 | 13.55 | 0.68 | 5.23 | 0.16 |
| F87 | 9.22 | 1.32 | 176.4 | 10.2 | 34.27 | 2.67 | 6.17 | 0.46 | 3.17 | 0.11 |
| F88 | 8.49 | 0.79 | 167.1 | 9.9 | 23.61 | 2.34 | 4.75 | 0.29 | 2.98 | 0.10 |
| F98 | 8.80 | 0.96 | 178.0 | 12.4 | 21.25 | 2.31 | 4.40 | 0.37 | 2.73 | 0.09 |
| F127 | 9.15 | 0.97 | 181.0 | 9.6 | 22.84 | 1.51 | 4.64 | 0.24 | 2.87 | 0.09 |
| P84 | 9.50 | 0.47 | 182.1 | 4.6 | 44.85 | 1.16 | 7.63 | 0.26 | 3.44 | 0.10 |
| P104 | 8.93 | 0.87 | 182.3 | 9.8 | 41.15 | 1.79 | 6.97 | 0.23 | 3.26 | 0.06 |
| 10R5 | 9.09 | 1.26 | 172.0 | 9.4 | 37.74 | 4.75 | 6.83 | 0.50 | 3.54 | 0.13 |
| 17R2 | 8.14 | 0.52 | 169.6 | 5.1 | 32.03 | 3.03 | 6.02 | 0.36 | 3.24 | 0.05 |
| 17R4 | 9.26 | 0.75 | 167.6 | 6.0 | 33.98 | 4.75 | 6.35 | 0.52 | 3.61 | 0.10 |
| 25R2 | 8.36 | 0.72 | 171.2 | 7.1 | 32.36 | 4.42 | 6.06 | 0.51 | 3.28 | 0.12 |
| 25R4 | 8.57 | 0.51 | 177.1 | 7.4 | 29.60 | 3.26 | 5.63 | 0.41 | 3.03 | 0.09 |
| 31R1 | 9.45 | 0.86 | 174.5 | 6.4 | 37.60 | 6.59 | 6.70 | 0.80 | 3.50 | 0.23 |
| ctrl | 9.55 | 0.60 | 161.7 | 6.8 | 49.45 | 7.22 | 8.43 | 0.92 | 4.31 | 0.30 |

Six mm disks from three separate slabs per lot of material were prepared for microvacuole testing. Disks were placed into 20 mL vials containing ~20 mL deionized water and incubated in a water bath at 45° C. for 24 hours. The sample vials were removed from the water bath and placed on the lab bench to cool to room temperature, typically 22-24° C. Each disk was imaged using an Olympus BX60 microscope under bright field (BF) and dark field (DFA) settings at 10× with a 2× magnifier. Samples were imaged after 4 hours and again after 2 weeks at 22-24° C. The results are shown in Tables 4 and 5. The abbreviation "nd" in Tables 4 and 5 means "none detected."

TABLE 4

MV testing post 4 hrs at ~22° C.

| Sample | Clarity | MV size | MV frequency | Optic field | # disks with MVs |
|---|---|---|---|---|---|
| L31 | haze | tiny/large | clusters | DFA | 3 |
| L43 | haze | tiny/large | clusters | DFA | 3 |
| L61 | haze, surface | — | — | — | — |
| L64 | sl haze | tiny/large | clusters | DFA | 3 |
| L81 | haze | tiny | full | DFA | 3 |
| L92 | haze, surface | — | — | DFA/BF | — |
| L101 | haze, surface | — | — | DFA/BF | — |
| F87 | clear | nd | nd | DFA | 0 |
| F88 | clear | nd | nd | DFA | 0 |
| F98 | sl haze | very tiny | full | DFA | 3 |
| P127 | clear | nd | nd | DFA | 0 |
| P84 | sl haze | very tiny | full | DFA | 3 |
| P104 | clear | nd | nd | DFA | 0 |
| 10R5 | haze | small | regional | DFA | 3 |
| 17R2 | haze | small | regional | DFA | 3 |
| 17R4 | sl haze | small | few | DFA | 3 |
| 25R2 | haze, surface | — | — | — | — |
| 25R4 | clear | nd | nd | DFA | 0 |
| 31R1 | haze, surface | — | — | — | — |
| ctrl | haze | very small | full | DFA | 3 |

TABLE 5

MV testing post 2 weeks at ~22° C.

| Sample | Clarity | MV size | MV frequency | Optic field | # disks with MVs |
|---|---|---|---|---|---|
| L31 | sl haze | large | clustered | DFA | 3 |
| L43 | v. sl. Haze | large | 1-2 per disk | DFA | 2 |
| L61 | haze, surface | — | — | — | — |
| L64 | v. sl. Hae | tiny/large | clustered/1-2 | DFA | 3 |
| L81 | haze, surface | tiny | full | DFA | 3 |
| L92 | haze, surface | — | — | DFA | — |
| L101 | haze, surface | — | — | DFA | — |
| F87 | clear | v. tiny | v. few | DFA | 2 |
| F88 | clear | v. tiny | many | DFA | 3 |
| F98 | sl haze | v. tiny | full | DFA | 3 |
| F127 | v. sl. haze | nd | nd | DFA | 0 |
| P84 | v. sl. haze | v. tiny | full | DFA | 3 |
| P104 | clear | nd | nd | DFA | 0 |
| 10R5 | clear | tiny | regional | DFA | 3 |
| 17R2 | clear | large | regional | DFA | 1 |
| 17R4 | clear | large | very few | DFA | 1 |
| 25R2 | haze, surface | — | — | — | — |
| 25R4 | clear | nd | nd | DFA | 0 |
| 31R1 | haze, surface | — | — | — | — |
| ctrl | clear | large | regional | DFA | 3 |

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:
1. An ophthalmic device material comprising
a) device-forming monomers consisting essentially of a single polymerizable monomer of the structure:

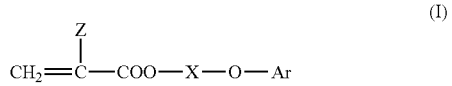

wherein:
Z is H or $CH_3$;
X is $(CH2)_m$ or $O(CH_2CH_2O)_n$;
m is 2-6;
n is 1-6; and
Ar is phenyl which can be unsubstituted or substituted with CH3, C2H5, n-C3H7, iso-C3H7, OCH3, C6H11, Cl, Br, C6H5, or CH2C6H5;
b) a polymerizable cross-linking agent; and
c) a non-polymerizable block copolymer surfactant selected from the group consisting of: a propylene oxide-ethylene oxide-propylene oxide block copolymer surfactant having an average molecular weight of approximately 3600 and an ethylene oxide unit content of approximately 40% by weight, and an ethylene oxide-propylene oxide-ethylene oxide block copolymer surfactant having an average molecular weight of approximately 5900 and a ethylene oxide unit content of approximately 40% by weight.

2. The ophthalmic device material of claim 1 wherein the monomer of structure (I) is selected from the group consisting of: 2-phenoxyethyl acrylate; 3-phenoxypropyl acrylate; 4-phenoxybutyl acrylate; polyethylene glycol phenyl ether acrylate; and their corresponding methacrylates.

3. The ophthalmic device material of claim 1 wherein X is $(CH_2)_m$; m is 2-4; and Ar is phenyl.

4. The ophthalmic device material of claim 3 wherein the single monomer of structure (I) is 2-phenyloxyethyl acrylate.

5. The ophthalmic device material of claim 1 wherein the amount of monomer of structure (I) is at least 75% by weight.

6. The ophthalmic device material of claim 5 wherein the amount of monomer of structure (I) is 80-90% by weight.

7. The ophthalmic device material of claim 6 wherein the amount of monomer of structure (I) is 87-90% by weight.

8. The ophthalmic device material of claim 5 wherein the amount of non-polymerizable block copolymer surfactant is 5-15% by weight.

9. The ophthalmic device material of claim 8 wherein the amount of non-polymerizable block copolymer surfactant is 9-11% by weight.

10. The ophthalmic device material of claim 1 wherein the non-polymerizable block copolymer surfactant is a propylene oxide-ethylene oxide-propylene oxide block copolymer surfactant having an average molecular weight of approximately 3600 and an ethylene oxide unit content of approximately 40% by weight.

11. The ophthalmic device material of claim 1 wherein the non-polymerizable block copolymer surfactant is an ethylene oxide-propylene oxide-ethylene oxide block copolymer surfactant having an average molecular weight of approximately 5900 and an ethylene oxide unit content of approximately 40% by weight.

12. The ophthalmic device material of claim 1 further comprising an ultraviolet absorbing compound.

13. The ophthalmic device material of claim 1 further comprising a yellow dye.

14. An ophthalmic device comprising the ophthalmic device material of claim 1, wherein the ophthalmic device is selected from the group consisting of: intraocular lenses; contact lenses; keratoprostheses; intracorneal lenses; and corneal inlays or rings.

* * * * *